United States Patent
Barnes et al.

[11] Patent Number: 5,894,964
[45] Date of Patent: Apr. 20, 1999

[54] AEROSOL

[75] Inventors: Howard Anthony Barnes, Wirral; Norman Clark, Wetherby; Michael Richard Lowry, Chester, all of United Kingdom

[73] Assignee: Chesebrough-Pond's USA Co., Division of Conopco, Inc., Greenwich, Conn.

[21] Appl. No.: 09/017,073

[22] Filed: Feb. 2, 1998

Related U.S. Application Data

[63] Continuation of application No. 08/531,801, Sep. 21, 1995, abandoned.

[30] Foreign Application Priority Data

Sep. 23, 1997 [GB] United Kingdom ............. 9419269

[51] Int. Cl.[6] ............................................. B65D 83/20
[52] U.S. Cl. .................. 222/402.1; 239/337; 239/590; 222/402.13
[58] Field of Search ...................... 239/337, 589, 239/590; 222/402.1, 402.13

[56] References Cited

U.S. PATENT DOCUMENTS

| | | |
|---|---|---|
| 3,108,590 | 10/1963 | Gorman . |
| 3,299,960 | 1/1967 | Stern ....................... 239/373 X |
| 3,428,223 | 2/1969 | Lewiecki et al. ............. 222/398 |
| 3,428,233 | 2/1969 | Lewiecki et al. . |
| 3,587,942 | 6/1971 | Gailitis . |
| 3,622,052 | 11/1971 | Gach . |
| 4,013,231 | 3/1977 | Van Veldhoven . |
| 4,125,499 | 11/1978 | Howard . |
| 4,187,204 | 2/1980 | Howard . |
| 4,650,094 | 3/1987 | Werding . |
| 5,213,266 | 5/1993 | Lankinen . |
| 5,480,095 | 1/1996 | Stevenson et al. ......... 222/402.1 X |

FOREIGN PATENT DOCUMENTS

| | | |
|---|---|---|
| 2 141 455 | 6/1971 | France . |
| 28 37 412 | 8/1978 | Germany . |
| 2 255 731 | 11/1992 | United Kingdom . |
| WO 86/01787 | 3/1986 | WIPO . |
| WO 88/03419 | 5/1988 | WIPO . |
| WO 95/07850 | 3/1995 | WIPO . |

Primary Examiner—Kenneth Bomberg
Attorney, Agent, or Firm—Milton L. Honig

[57] ABSTRACT

An aerosol actuator is provided having an inner actuator chamber, an inner actuator chamber outlet by which the composition to be dispensed may exit the inner actuator chamber, and a stem piece channel by which the fluid to be dispensed may enter the inner actuator chamber. The inner surface of the inner actuator chamber is mathematically continuous. The mathematically continuous arrangement minimizes nozzle blockage in the actuator.

5 Claims, 3 Drawing Sheets

AEROSOL

This is a continuation of Ser. No. 08/531,801 filed Sep. 21, 1995 now abandoned.

BACKGROUND OF THE INVENTION

1. Field of the Invention

This invention relates to aerosol dispensers and packaged aerosol compositions which are suitable for topical use. In particular, it relates to aspects of the aerosol hardware which makes the dispenser particularly suitable for spraying aerosol compositions which contain particulate material, and to topical compositions containing particulate material for packaging therein.

2. The Related Art

It has long been appreciated that a problem with spraying topical compositions containing particulate material is that there is a tendency for such aerosol products to suffer excessive nozzle blockage. This results in the user being unable to discharge the product from the aerosol container fully, with the result that the user is often left with some product in the container they are unable to dispense.

A variety of solutions have been adopted to overcome this problem, some involving modification of the aerosol hardware, whilst others have involved modification of the formulation being sprayed. For example, GB 2 029 441 describes a powder aerosol composition comprising a suspension of 5 to 60% by weight of powder, 5 to 80% of short chain alcohol and 5 to 80% water, together with 5 to 40% propellant having a specific gravity lower than the suspension. This composition is said to be designed to facilitate redispersion, and therefore minimise the rate of agglomeration and nozzle clogging.

CA 1 106 329 addresses the same technical problem specifically in the field of suspension antiperspirant compositions, and alleges to overcome it by providing a suspension aerosol system incorporating a large amount of powdered antiperspirant active distributed in a substantially anhydrous oil system, which in turn is suspended in relatively small quantities of propellant. This composition in turn is dispensed from an aerosol container having a metered valve, which delivers uniform dosages of antiperspirant composition in use.

It has also been observed that any problems observed with blockage in a powder aerosol product tend to be exaggerated if the spray rate is relatively low. Typical spray rates for powder aerosols are in the region 0.7–1.2 $gs^{-1}$ at 25° C. We have found the problem to be particularly acute if the spray rate is taken below this, for example to levels in the region 0.25–0.6 $gs^{-1}$ at 25° C. The problems are also exaggerated if the solids content of the spray composition is high; that is if the composition (inclusive of propellant) contains more than about 4% suspended solids, in particular more than about 10% suspended solids.

From our detailed study of trying to improve the spray characteristics of powder compositions, particularly with a view to decreasing the rate of blockage suffered by powder aerosols, we have found that certain hardware aspects of the aerosol dispenser are important in minimising the blockage rate.

A typical aerosol dispenser comprises a diptube which is attached to a valve assembly by means of a restricted tail piece. The valve assembly typically has one or more vapour phase taps, which permit propellant gas to enter the valve assembly, where it mixes with the composition to be sprayed, which is delivered to the valve assembly by the diptube. The valve assembly also typically has a generally open end, which is generally sealed by a gasket and a closure piece on the stem, which seals the orifice in the gasket. The closure piece on the stem is generally biased to the closed position by the action of a spring located within the valve assembly.

Above the closure piece on the stem are one or more stem orifices, which are located generally towards the bottom of the stem. When the valve is not in use, these stem orifices are not in fluid communication with the valve assembly. The stem leads generally to an actuator button, which itself typically has an input orifice for the stem, an inner actuator chamber, and a terminal orifice through which sprayed fluid exits when the aerosol container is used.

In use, pressure by the user on the top of the actuator button causes the stem to depress. The closure piece of the stem acts on and compresses the spring in the valve assembly. Depression of the stem brings the stem orifice(s) into liquid contact with the valve assembly, whereby a mixture of gaseous propellant and liquid to be sprayed is driven through the stem orifice(s) and up the stem. The mixture subsequently enters the inner actuator chamber, and then exits the actuator via the terminal orifice.

SUMMARY OF THE INVENTION

We have found that significant improvements can be made in nozzle blockage rates if the spray nozzle actuator is configured in a particular fashion. In particular, it is highly preferred that the inner actuator chamber of the nozzle actuator has a small volume, being minimised as much as possible. In addition, we have found it preferable that the inner actuator chamber is configured in certain ways to try to optimise the flow of sprayable material through it.

Thus, in the broadest aspect of the invention, there is provided an aerosol actuator having an inner actuator chamber, an inner actuator chamber outlet by which the composition to be dispensed may exit the inner actuator chamber, and a stem piece channel by which the fluid to be dispensed may enter the inner actuator chamber, characterised in that the inner surface of the inner actuator chamber is mathematically continuous.

According to a further aspect of the invention, there is provided an aerosol actuator having an inner actuator chamber, an inner actuator chamber outlet by which the composition to be dispensed may exit the inner actuator chamber, the inner actuator chamber outlet having an outlet axis, and a stem piece channel, by which the fluid to be dispensed may enter the inner actuator chamber, the stem piece channel having a stem axis, both the inner actuator chamber outlet and the stem piece channel being substantially circular in cross section, the outlet axis being located substantially perpendicularly to the stem axis, the closest approximation of stem axis to the outlet axis being the actuator point, the inner actuator chamber not extending more than the radius of the stem piece channel along the outlet axis from the actuator point in the direction opposite the inner actuator chamber outlet, the inner actuator chamber not extending more than five times the radius of the inner actuator chamber outlet from the actuator point along the stem axis in the direction opposite the stem piece channel, the inner surface of the inner actuator chamber being mathematically continuous.

By "mathematically continuous" is meant that all derivatives of the mathematical function describing the inner surface of the inner actuator chamber are continuous. Hence the surface has no discontinuities, and in particular no angled discontinuities such as corners or edges, which provide a sharp change in the angle of the surface.

It is a highly preferred embodiment of the above two aspects of the invention that the inner surface of the inner actuator chamber is mathematically continuous with the inner surface of the stem piece channel, which itself is mathematically continuous. In certain embodiments, it is also preferred that the inner surface of the inner actuator chamber is mathematically continuous with the inner surface of the inner actuator chamber outlet, which itself is mathematically continuous, though embodiments of the invention are envisaged where this is not so—i.e. that there is one or more angled discontinuities, such as edges or corners in the nozzle actuator where the inner actuator chamber meets the inner actuator chamber outlet.

Conveniently, the inner actuator chamber outlet may be adapted to accommodate a terminal orifice insert; this is particularly so for so-called two piece actuators.

According to the invention, the substantially circular cross section inner actuator chamber outlet and stem piece channel may include circular outlets or channels, or the same being elliptical with the ratio of major to minor axes being less than 1.2:1. The inner actuator chamber outlet and stem piece channel may also be generally irregular in cross section, for example, having an egg shaped cross section. In such instances, likewise the ratio of the maximum width of the outlet or channel to the maximum depth of the outlet or channel will be less than 1.2:1. The reference to "radius" in such circumstances is also to be construed as half the maximum width or depth of the outlet or channel, or the minor and major axes of the ellipse, as appropriate.

It is highly preferred that the actuator of the first aspect of the invention be used in conjunction with powder containing aerosols. Thus, according to a further aspect of the invention, there is provided a packaged aerosol composition for topical application, comprising a suspension of a powder in a liquified propellant gas and a cosmetically suitable vehicle, packaged in a pressurized container having an aerosol actuator having an inner actuator chamber, an inner actuator chamber outlet by which the composition to be dispensed may exit the inner actuator chamber, and a stem piece channel by which the fluid to be dispensed may enter the inner actuator chamber, characterised in that the inner surface of the inner actuator chamber is mathematically continuous.

In a more detailed aspect, there is provided a packaged aerosol composition for topical application, comprising a suspension of powder in a liquified propellant gas and a cosmetically suitable vehicle, packaged in a pressurised container having an aerosol actuator having an inner actuator chamber, an inner actuator chamber outlet by which the composition to be dispensed may exit the inner actuator chamber, the inner actuator chamber outlet having an outlet axis, and a stem piece channel, by which the fluid to be dispensed may enter the inner actuator chamber, the stem piece channel having a stem axis, both the inner actuator chamber outlet and the stem piece channel being substantially circular in cross section, the outlet axis being located substantially perpendicularly to the stem axis, the closest approximation of stem axis to the outlet axis being the actuator point, the inner actuator chamber not extending more than the radius of the stem piece channel along the outlet axis in the direction opposite the inner actuator chamber outlet from the actuator point, the inner actuator chamber not extending more than five times the radius of the inner actuator chamber outlet along the stem axis in the direction opposite the stem piece channel from the actuator point, the inner actuator chamber having an inner surface which is mathematically continuous.

Preferably the stem axis of the stem piece channel and the outlet axis of the inner actuator chamber outlet will not just approximate to each other at the actuator point, but will actually coincide there. When this happens, the stem piece channel and the inner actuator chamber outlet are in the same plane.

It is also preferred that the outlet axis and the stem axis are substantially perpendicular; however they may make an angle with each other of up to 110°.

In the embodiments of the invention contemplated, the stem piece channel part in the actuator commences adjacent to where the stem piece of the pressurised container extends to in the actuator, when the actuator is fitted onto the stem piece. Thus where so called male stems fit into a so called female actuator, the stem piece channel of the actuator commences immediately adjacent where the stem piece ends when the actuator is fitted on the stem piece. Where however a so called male actuator is fitted onto a female valve assembly, the stem piece channel on the actuator begins at the closest approach of the end of the stem piece to the inner surface of the actuator.

It is also envisaged that in some embodiments of the invention the stem piece channel will run directly into the inner actuator chamber, with no obvious boundary between the two.

Preferably, the packaged aerosol composition is an antiperspirant composition and the powder in the aerosol composition may comprise suspended antiperspirant active salts, such as aluminium salts, or inert filler materials, such as talc, corn starch, or micronised polyethylene particles, or mixtures thereof. Preferably, in such compositions the suspended powder comprises 5–40% by weight of the composition.

In such compositions, the balance of the composition comprises a liquid propellant and a cosmetically suitable vehicle. Suitable propellants include dimethylether, pentane, difluorochloromethane, tetrafluoroethane, trichlorofluoromethane, trichlorofluoroethane, difluoroethane, propane, isopentane, isobutane or butane, used singly or in combination. The propellant may typically comprise 15–95% of the packaged composition; however actuators according to the invention may be particularly useful in compositions containing relatively low amounts of propellant; that is less than 60% by weight of propellant, preferably 40–60% by weight of propellant.

The balance of the composition may comprise any of the ingredients typically found in a packaged antiperspirant aerosol composition, including;

linear or cyclic volatile silicones, including polydimethyl siloxanes such as Dow Corning 344 Fluid and Dow Corning 345 Fluid, and volatile hexamethyldisiloxane such as Dow Corning 200 Fluid, non-volatile silicones, including polydimethylsiloxane, such as Dow Corning Fluids, short chain monohydric alcohols such as ethanol and isopropanol, skin feel improvers, including particulate materials such as talc and finely divided polyethylene, for example Acumist B18, cosmetically acceptable vehicles, glycerol, glycols such as propylene glycol or butylene glycol, and emollients, gelling agents, such as stearyl alcohol, sodium stearate or waxes, such as castor wax, preservatives, and other cosmetically acceptable adjuncts conventionally employed in propellant driven spray antiperspirant products.

In particular when the packaged composition is an antiperspirant composition, preferably the composition is essentially anhydrous—i.e. it comprises less than 0.1% water.

The balance of the composition formed by these optional components may typically be in the region of 10–50% of the composition.

BRIEF DESCRIPTION OF THE DRAWING

The invention will now be described by way of example only, in which.

DETAILED DESCRIPTION OF THE INVENTION

Figure 1:
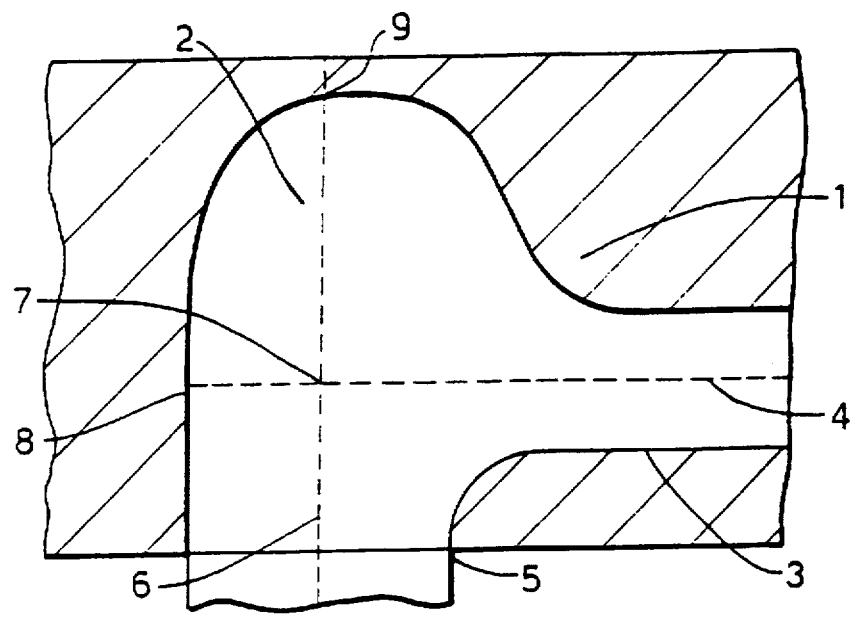
FIG. 1 represents a schematic cross sectional view of an actuator geometry according to the invention.

FIG. 1 illustrates schematically the internal geometry of an actuator according to the invention, suitable for attachment to an otherwise conventional pressurized aerosol dispensing apparatus. The general body of the actuator housing is represented by 1, in which is shown inner actuator chamber 2. Inner actuator chamber 2 has an inner actuator chamber outlet 3, which is adapted to accommodate a terminal orifice (not shown), by which the sprayed composition exits the pressurized container in use.

Inner actuator chamber outlet 3 is circular in cross section, having a diameter of 1 mm, and a button orifice diameter of $18/1000$ inch (0.46 mm). Inner actuator-chamber outlet 3 has an outlet axis (dotted line 4), which runs axially in the longitudinal direction of the outlet, at a distance of half the diameter from the sides of outlet 3.

Inner actuator chamber 2 also has a stem piece channel 5, which may be attached so as to be fluid communication with the stem of an aerosol valve on a pressurised container (not shown). Stem piece channel 5 is circular in cross section and of 2 mm diameter, and acts to allow fluid from the pressurized aerosol container to access the inner actuator chamber 2, once it passes through the stem of the aerosol valve. Stem piece channel 5 has a stem axis (dotted line 6), which runs axially along stem piece channel 5.

In this embodiment outlet axis 4 and stem axis 6 coincide at point 7, known as the actuator point. It is an essential feature of this embodiment that the inner surface of inner actuator chamber is mathematically continuous, and as such has a smooth surface, with no angled discontinuities, such as corners or edges, with all inner surfaces of the inner actuator chamber being well rounded.

In addition, it is also a feature of this embodiment that the back surface of the inner actuator chamber extends no further from actuator point 7 than point 8, which represents the radius of the stem piece channel from the actuator point 7, running in a direction which is 180° from the inner actuator chamber outlet 3, along the outlet axis 4.

However, the inner actuator chamber 2 extends upwards from the actuator point 7 to point 9, a distance of approximately 4.3 times the radius of the inner actuator chamber outlet 3 in a direction 180° to the direction of the stem piece channel, along the stem axis 6.

Whilst it is a preferred feature that the inner actuator chamber 2 extends upwards along the stem axis 6 a distance of less than 5 times the radius of the outlet channel 3, this distance may conveniently be between 0.5 and 4.5 times the radius of the outlet channel, preferably between 0.5 and 2.5 times the radius of the outlet channel. In all embodiments though, the inner surface of inner actuator chamber 2 must be free of angled discontinuities, and be well rounded.

In addition, it is preferred that the inner actuator chamber has a volume of less than about 20 mm$^3$. Also, it is preferable that the inner actuator chamber extends along the stem axis in the direction opposite the stem piece channel for a distance less than 2.5 mm, more preferably less than 2 mm, even more preferably less than 0.6 mm from the actuator point.

An actuator with an inner actuator chamber configuration as shown and described in FIG. 1 can be made from plastics materials using molding techniques.

Figure 2:
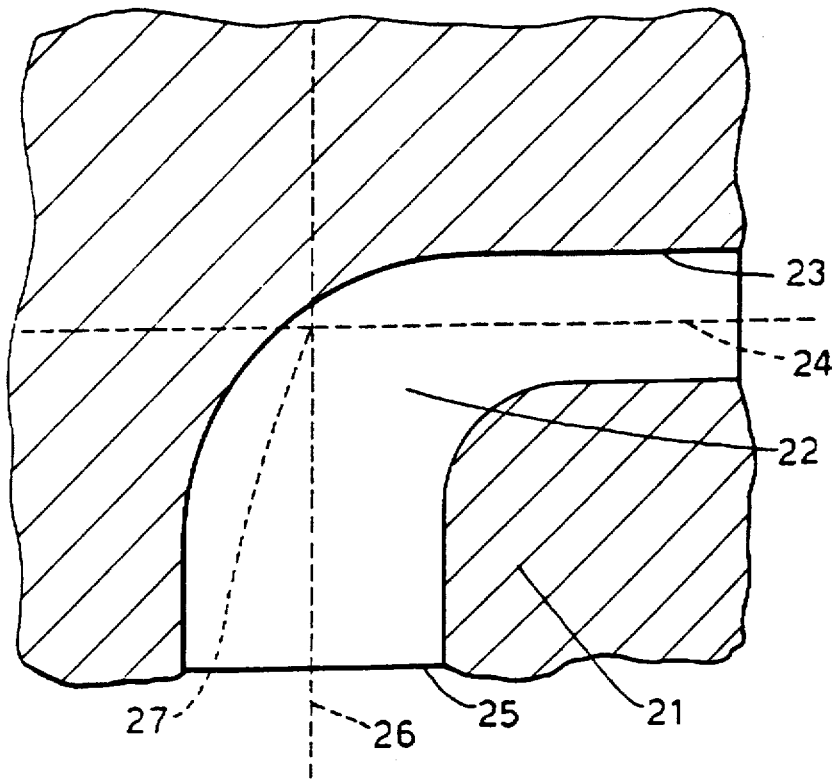
FIG. 2 represents a schematic cross sectional view of a further actuator geometry according to the invention.

FIG. 2 shows schematically a further inner actuator chamber geometrically according to the invention.

Like the actuator of FIG. 1, the actuator of FIG. 2 has a general body 21, in which is located inner actuator chamber 22. Inner actuator chamber 22 has an inner actuator chamber outlet 23 which is circular in cross section and of 1 mm diameter, which is adapted to accommodate a button orifice (not shown) of 0.46 mm diameter. Outlet axis 24 runs in the longitudinal direction of the outlet 23, at a distance half the diameter from the sides of outlet 23.

Stem piece channel 25 may be attached in series with the stem of an aerosol valve on a pressurised container, to allow the fluid to be sprayed to access the inner actuator chamber 22, and is circular in cross section, being of 2 mm diameter. Stem axis 26 runs axially along stem piece channel 25. Stem axis 26 and outlet axis 24 meet at actuator point 27. In this embodiment, the inner actuator chamber 22 extends upwards from the actuator point approximately 0.5 times the radius of the outlet channel 23 along the stem axis, while it also extends back approximately 0.4 the radius of the stem piece channel 25 from actuator point 27, along the outlet axis 24.

In embodiments of the invention when the actuator has a terminal orifice, the orifice preferably has a diameter of 13–22/1000 inch (0.33–0.56 mm), more preferably 16–18/1000 inch (0.41–0.46 mm), most preferably 18/1000 inch (0.46 mm). The actuator according to the invention may be adapted to be used in conjunction with pressurized containers having any stem piece diameter which is used in the art.

In the embodiments of FIGS. 1 and 2, not only is the inner surface of the inner actuator chamber mathematically continuous, but so are the inner surfaces of the stem piece channel, the inner actuator chamber outlet, and the boundaries therebetween.

An actuator with an inner actuator chamber configuration as shown and described in FIG. 2 can be made from plastics materials using molding techniques.

Figure 3:
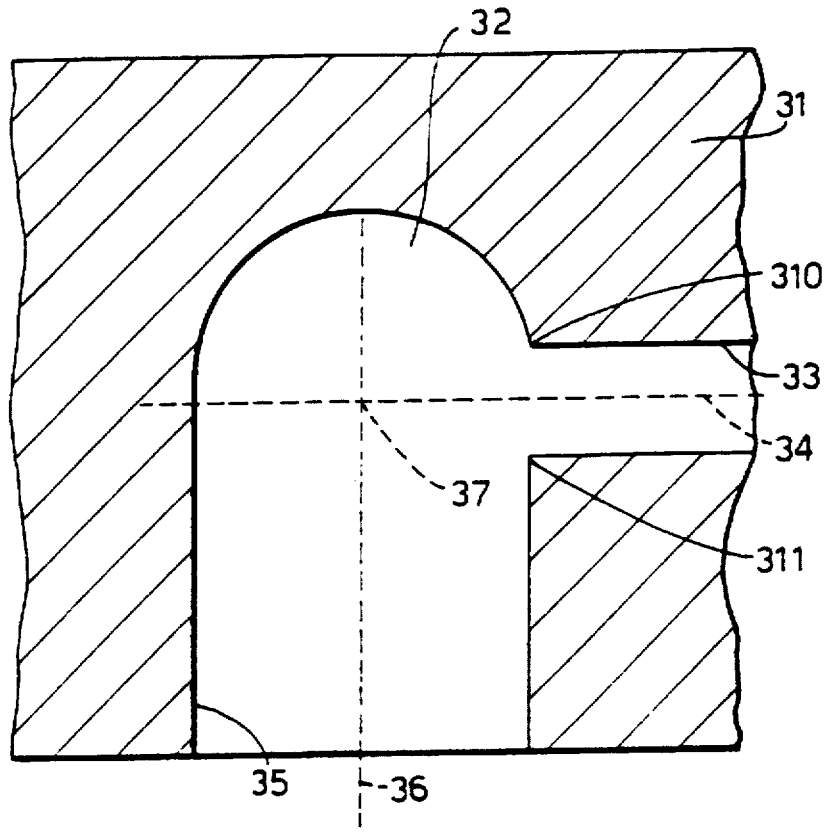
FIG. 3 represents a schematic cross sectional view of a further actuator geometry according to the invention.
Figure 4:
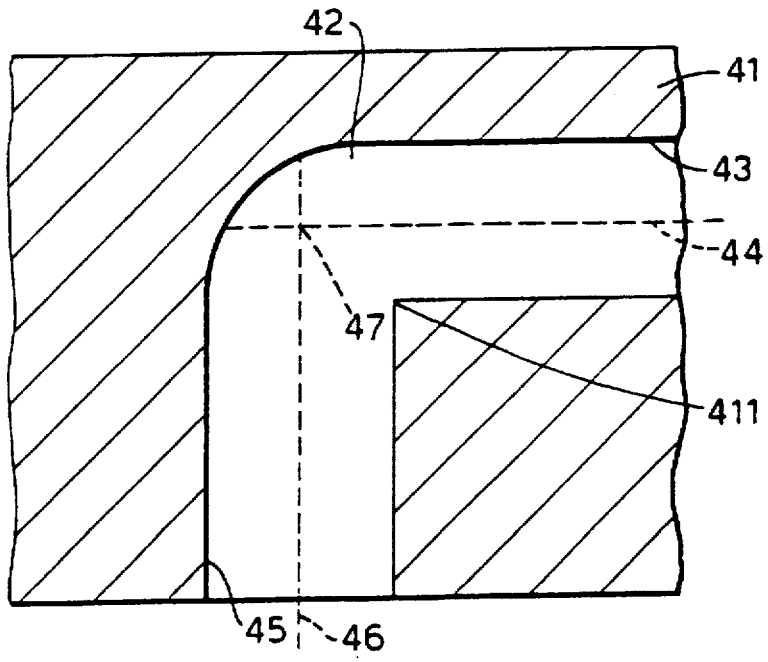
FIG. 4 represents a schematic cross sectional view of yet a further actuator geometry according to the invention and FIG. 5 is a schematic cross-sectional of an aerosol dispenser actuator containing an actuator geometry according to FIG. 1.

FIGS. 3 and 4 shows schematic cross sectional views of further embodiments of the invention.

Regarding FIG. 3, and as with previous embodiments, the actuator geometry of FIG. 3 has a general body 31, in which is located inner actuator chamber 32. Inner actuator chamber outlet 33 is circular in cross section, along the centre of which runs outlet axis 34. Inner actuator chamber 32 also has depending from it stem piece channel 35, which is circular in cross section, and which has a stem axis 36. As with the embodiments of FIGS. 1 and 2, stem piece channel 35 is essentially integral with inner actuator chamber 32, the inner surfaces of the stem piece channel 35 and inner actuator chamber 32 and the boundary between them being mathematically continuous.

Stem axis 36 and outlet axis 34 coincide at actuator point 37, with the inner actuator chamber 32 extending upwards approximately 4.2 times the radius of inner actuator chamber outlet 33 along stem axis 36, whilst it also extends back approximately the radius of stem piece channel 35 along outlet axis 34.

In contrast to the previous embodiments though, the inner surface of inner actuator chamber 32 is not mathematically continuous with the inner surface of inner actuator chamber outlet 34. That is, there are angled discontinuities, 310 and 311, between the respective inner surfaces.

Concerning FIG. 4, the actuator geometry has an analogous general body 41, inner actuator chamber 42, circular cross-section inner actuator chamber outlet 43 with outlet axis 44, and circular cross-section stem piece channel 45 with stem axis 46. In this embodiment and like that of FIG. 3, stem piece channel 45 is essentially integral with inner actuator chamber 42, the inner surfaces of stem piece channel 45 and inner actuator chamber 32 being mathematically continuous.

Stem axis 46 and outlet axis 44 coincide at actuator point 47, with the inner actuator chamber 42 extending upwards approximately 0.9 times the radius of inner actuator chamber outlet 43 along stem axis 46, whilst also extending back approximately 0.9 times the radius of stem piece channel 45 along outlet axis 44.

As with the embodiment in FIG. 3, the inner surface of inner actuator chamber 42 is not mathematically continuous with the inner surface of inner actuator chamber outlet 34, there being an angled discontinuity 411 between the respective inner surfaces.

The embodiments of FIGS. 3–4 are manufacturable by routine injection moulding techniques from plastics materials by those skilled in the art.

Figure 5:
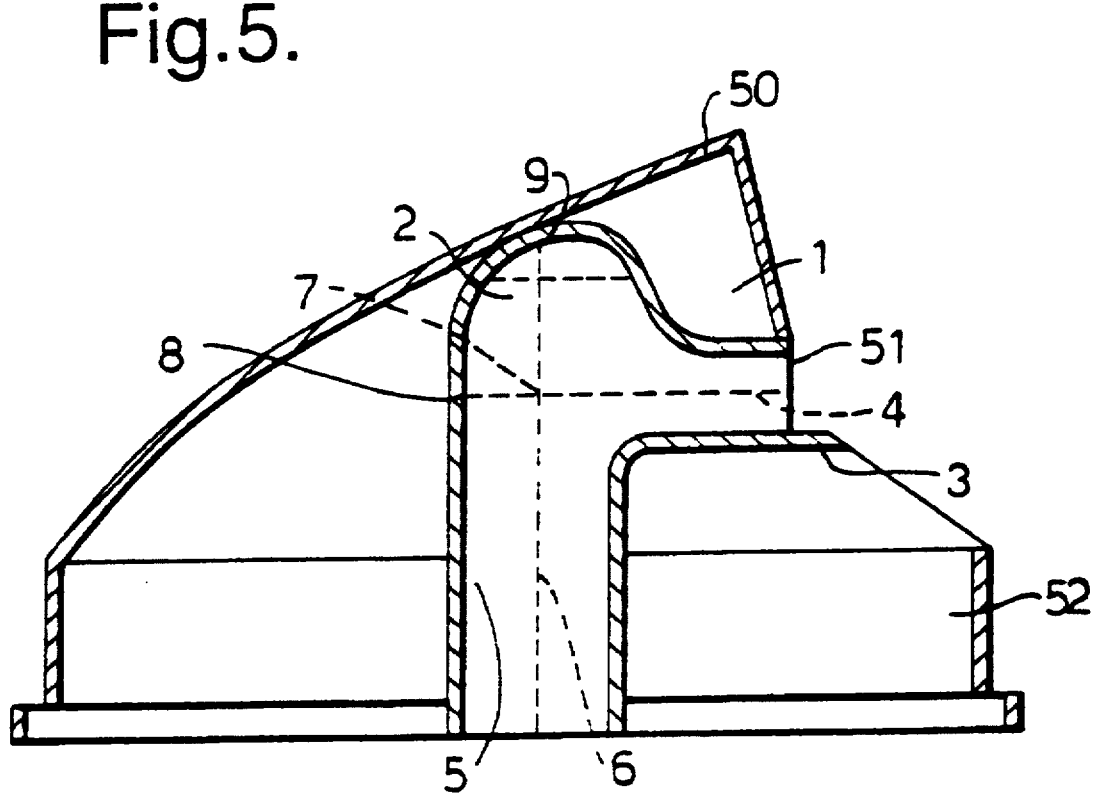

FIG. 5 shows a schematic cross-sectional view of an aerosol dispenser actuator having an actuator geometry as described in relation to FIG. 1 above.

As shown in the drawing, the actuator is made up of an actuator housing 1 fitted with an inner actuator 2, and inner actuator chamber outlet 3, and a stem piece 5. The axes represented by dotted lines 4 and 6 are arranged as previously described while the points 7, 8 and 9 are also arranged as previously described in FIG. 1.

The inner actuator chamber 2 is surrounded by the actuator housing 1 made up of an actuator button 50 which is depressed to cause fluid to exit through the inner actuator chamber 2. Depression of the actuator button 50 causes fluid to enter the inner actuator chamber 2 and to exit there from through the inner actuator chamber outlet 3.

The housing 1 has a skirt portion 52 which engages with the neck of an aerosol container body (not shown).

In use, depression of the actuator button 50 causes aerosol mixture to enter the inner actuator chamber 2 and which subsequently exits the actuator via a terminal orifice 51.

The inner actuator chamber volume is minimised such that nozzle blockage rates are reduced. Moreover, the continuous inner wall of the inner actuator chamber 2 further minimizes deposition within the actuator chamber thereby eliminating blockages.

We claim:

1. An aerosol actuator defined by a housing having an inner actuator chamber, an inner actuator chamber outlet by which a composition to be dispensed may exit the inner actuator chamber, the inner actuator chamber outlet having an outlet axis, and a stem piece channel, by which the composition to be dispensed may enter the inner actuator chamber, the stem piece channel having a stem axis, both the inner actuator chamber outlet and the stem piece channel being substantially circular in cross section, the outlet axis being located substantially perpendicularly to the stem axis, an intersection of the stem axis with the outlet axis defining an actuator point, the inner actuator chamber not extending more than a radius of the stem piece channel along the outlet axis in a direction opposite the inner actuator chamber outlet from the actuator point, the inner actuator chamber not extending more than 5 times a radius of the inner actuator chamber outlet along the stem axis in a direction opposite the stem piece channel from the actuator point, an inner surface of the inner actuator chamber being mathematically continuous with an inner surface of the inner actuator chamber outlet; and wherein the inner actuator chamber is dome shaped in a direction extending along the stem piece axis opposite to the stem piece channel.

2. An aerosol actuator according to claim 1, wherein the inner surface of the inner actuator chamber is mathematically continuous with an inner surface of the stem piece channel.

3. An aerosol actuator according to claim 1 wherein the inner actuator chamber extends from 2.5 to not more than 5 times the radius of the inner actuator chamber outlet along the stem axis in a direction opposite the stem piece channel from the actuator point.

4. An aerosol actuator according to claim 2 wherein the dome shaped inner actuator chamber extends in the direction of the outlet axis in the direction of the inner actuator chamber outlet by at least the radius of the stem piece channel.

5. An aerosol actuator according to claim 4 wherein the dome shaped inner actuator chamber has an axis substantially parallel to the stem piece axis.

* * * * *